United States Patent [19]

Ishikawa

[11] 4,043,335

[45] Aug. 23, 1977

[54] NEEDLE HOLDER DEVICE OF MEDICAL ADMINISTRATING INJECTOR

[76] Inventor: Soji Ishikawa, No. 6-305-18, 1-chome, Utsukushiga-oka, Midori Yokohama, Kanagawa, Japan

[21] Appl. No.: 714,264

[22] Filed: Aug. 13, 1976

[30] Foreign Application Priority Data

Aug. 23, 1975 Japan ............................... 50-116506
Mar. 11, 1976 Japan ............................... 51-28087

[51] Int. Cl.² ............................................ A61M 5/32
[52] U.S. Cl. ................................ 128/218 N; 128/221
[58] Field of Search ....... 128/218 N, 218 NV, 218 R, 128/221, 215, 216, 214 C, 214 R

[56] References Cited

U.S. PATENT DOCUMENTS

| 2,833,281 | 5/1958 | Krug | 128/221 |
| 2,857,913 | 10/1958 | Miskel | 128/221 |
| 2,864,366 | 12/1958 | Miskel | 128/221 |
| 3,757,780 | 9/1973 | Ishikawa | 128/218 N |

*Primary Examiner*—John D. Yasko

[57] ABSTRACT

A needle holder device for use in a medical administering injector such as a syringe or dripset, comprising a generally tubular member formed with a liquid conducting passageway consisting of two axially spaced cylindrical bore portions and a frusto-conical bore portion between the cylindrical bore portions, and a filter assembly held in position within one of the cylindrical bore portions and located in proximity to the frusto-conical bore portion, the filter assembly including at least one filter element and filter retaining means formed with open spaces providing communication between the frusto-conical bore portion through the filter element and one of the cylindrical bore portions, the retaining means including at least one conical or otherwise tapered axial projection extending into at least one of the cylindrical bore portions.

36 Claims, 13 Drawing Figures

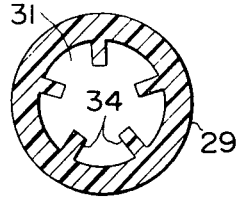
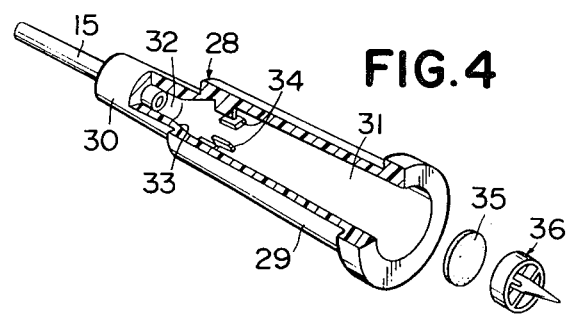
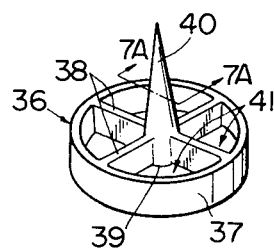 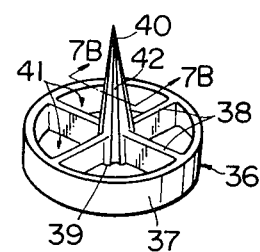
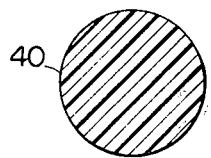 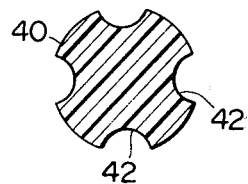
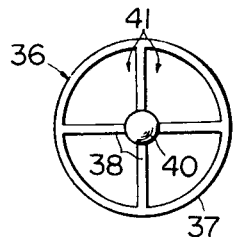 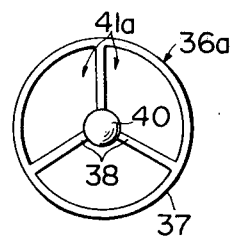

NEEDLE HOLDER DEVICE OF MEDICAL ADMINISTRATING INJECTOR

The present invention relates to medical administering liquid injectors such as hypodermic, intramuscular or intravenous syringes and dripsets for injecting medical solutions or blood for transfusion into the bloodstreams or other tissues of human or animal body and, more particularly, to a needle holder device forming such a liquid injector.

When in handling syringes or dripsets for medical administering operation or during production or transit of such devices, there are a variety of possibilities that solid impurities may be admitted into the syringes or dripsets or into the medical solutions stored therein or the blood which has been introduced thereinto. These impurities will include not only the dust or fine particles which have ingressed into the syringes or dripsets from external sources but the fine fragments of glass or rubber which are produced when an ampoule or other breakable container of a medical solution is cut open or during the process in which a rubber plug is fitted to the liquid reservoir or a liquid conducting tube of a medical administering dripset prior to administration. The solid impurities thus present in the medical solution or blood in a syringe or dripset will find their way through the needle holder device and the injection needle into the bloodstreams or other body tissues together with the solution or blood injected thereinto and may injure the vascular or other tissues.

Medical administering liquid injectors having filter media have therefore been proposed and put into use on a clinical basis for the purpose of removing solid impurities from the medical solution or the blood for intavenous transfusion before the solution or blood is discharged from syringes or dripsets. The filter medium is ordinarily held in position between the bores in the main body portion and tip portion of a needle holder device of a syringe or dripset and is thus operative to collect solid impurities from the medical solution or blood being passed from the bore in the main body portion into the bore in the tip portion, viz., at the substantial terminal end of the flow of the solution or blood through the syringe or dripset.

When a medical administering liquid injector of this nature is in use, the filter medium located in the main body portion of the needle holder device is subjected to a force urging the filter medium in either longitudinal direction in the needle holder device. When, for example, the needle holder device of a syringe is being used for drawing a liquid medicament from ampoule by pulling the piston of the syringe backwardly prior to administering operation, then the filter medium is urged away from the tip portion of the needle holder device by reason of the pressure of the liquid flowing from the tip portion into the body portion and the suction or partial vacuum developed behind the filter medium. When, on the contrary, the needle holder device of a syringe or dripset is being used for the injection of a medical solution or blood which has been introduced thereinto, the filter medium is then urged in the opposite direction, viz., toward the tip portion of the needle holder device by the pressure of the liquid flowing from the main body portion toward the tip portion. In whichsoever direction the filter medium may be thus urged, the filter medium tends to be deformed or dislodged from its original position relative to the needle holder device and to produce a fine gap between the outer peripheral edge of the filter medium and the inner peripheral surface of the main body portion. Such a tendency will be pronounced if a differential pressure is produced across the filter medium due to, for example, a difference between the cross sectional areas of the bore portions upstream and downstream of the filter medium. Formation of such a gap between the filter medium and the inner peripheral surface of the main body portion of a needle holder device provides communication between the bore portions on both sides of the filter medium and, as a consequence, the liquid in the bore portion upstream of the filter medium is allowed to bypass the filter medium and partially enter the bore portion downstream of the filter medium without being filtered. This causes critical deterioration of the filtration efficiency and the liquid discharged from the syringe or dripset will contain solid impurities which have failed to be collected by the filter medium. The present invention contemplates elimination of all these drawbacks inherent in needle holder devices of the conventional designs.

It is, accordingly, an object of the present invention to provide an improved needle holder device incorporating a filter assembly which is securely held in position and which is thus prevented from being deformed or dislodged from its original position even when the filter assembly is subjected to a forceful pressure or suction by the liquid passed therethrough during use of the needle holder device.

It is another object of the present invention to provide an improved needle holder device incorporating a filter assembly therein and having internal configurations adapted to significantly lessen or eliminate the differential pressure across the filter assembly.

In accordance with the present invention these objects will be accomplished basically in a needle holder device which comprises a generally tubular member formed with a longitudinal passageway extending between the opposite ends of the tubular member and consisting of a generally cylindrical first bore portion terminating at one end of the tubular member, a generally cylindrical second bore portion terminating at the other end of the tubular member and smaller in diameter than the first bore portion, the second bore portion being adapted to receive therein an end portion of an injection needle to be mounted on the holder device, and a generally frusto-conical third bore portion between the first and second bore portions and continuously reduced in diameter from its enlarged axial end adjacent the first bore portion toward its reduced axial end adjacent to the second bore portion, the first, second and third bore portions having respective center axes which are substantially in line with each other, and a filter assembly held in position within the first bore portion, the filter assembly including at least one filter element having its entire peripheral edge received on the inner peripheral surface of the tubular member and filter retaining means in contact with at least one end face of the filter element and formed with at least two providing communication between the first and third bore portions across the filter element, the filter retaining means including at least one conical projection extending in a direction parallel with the center axis of the first bore portion and passing through the center axis of the open spaces.

The above mentioned filter retaining means may comprise at least one filter retaining element including a circular rim portion having its outer peripheral edge on the inner peripheral surface of the tubular member and having a center axis, at least two radial limb portions extending radially inwardly from the rim portion and angularly spaced apart from each other about the center axis of the rim portion, a central portion containing the center axis of the rim portion and conjoining the radial limb portions, the rim portion, limb portions and central portion being in contact with one end face of the filter element and forming the aforesaid open spaces therebetween, the aforesaid conical projection axially extending from the central portion away from the filter element. In this instance, the tubular member may be further formed with a plurality of radial projections radially inwardly projecting into the first bore portion from the inner peripheral surface of the tubular member and circumferentially spaced apart from each other about the enter axis of the first bore portion, the radial projections having longitudinal ends on a common plane perpendicular to the center axis of the first bore portion and axially spaced apart from the enlarged axial end of the third bore portion, the radial projections receiving the filter assembly at the above mentioned longitudinal ends.

In one embodiment of the present invention, the above described filter means comprises first and second filter retaining elements spaced apart from each other and receiving the filter element therebetween, each of the first and second filter retaining elements including a circular rim portion having its outer peripheral end on the inner peripheral surface of the tubular member and having a center axis, at least two radial limb portions extending radially inwardly from the rim portion and angularly spaced apart from each other about the center axis of the rim portion, and a central portion containing the center axis of the rim portion and conjoining said radial lim portions, the rim portion, limb portions and central portion forming the previously mentioned open spaces therebetween on each side of the filter element, the aforesaid conical projection axially extending from the central portion of each filter retaining element away from the filter element, the conical projection of the first filter retaining element extending in the first bore portion and the conical projection of the second filter retaining element projecting into the third bore portion. In this instance, the tubular member may be further formed with a plurality of radial projections radially inwardly projecting into the first bore portion from the inner peripheral surface of the tubular member and circumferentially spaced apart from each other about the center axis of the first bore portion, the radial projections being longitudinally spaced apart from the enlarged axial end of the third bore portion a distance substantially equal to the thickness of the filter assembly and having first end faces closer to the third bore portion and second end faces remoter from the third bore portion, the filter assembly being held in position between the enlarged axial end of the third bore portion and the radial projections, the first filter element having one face in contact with one end face of the filter element and having its rim portion received on the radial projections at the first end faces thereof, the second filter retaining element having one end face in contact with the other end face of the filter element and the other end face located adjacent to the enlarged axial end of the third bore portion.

The features and advantages of a needle holder device according to the present invention will be understood more clearly from the following description taken in conjunction with the accompanying drawings in which like reference numerals designate corresponding members, elements and portions and in which:

FIG. 4 is a partially cut-away perspective view of the needle holder device illustrated in FIG. 3;

FIG. 5 is a cross-sectional view taken on line V—V of FIG. 3;

FIG. 6A is a perspective view showing, to an enlarged scale, the configuration of each of filter retaining elements incorporated into the embodiment illustrated in FIGS. 3 and 4;

FIG. 6B is a view similar to FIG. 6A but shows a modified configuration of the filter retaining element;

FIG. 7A is a section taken on line 7A—7A of FIG. 6A;

FIG. 7B is a section taken on line 7B—7B of FIG. 6B;

FIG. 8A is a plan view of the filter retaining element illustrated in FIG. 6A;

FIG. 8B is a plan view showing an alternative example of the filter retaining element illustrated in FIG. 8A;

Figure 1:
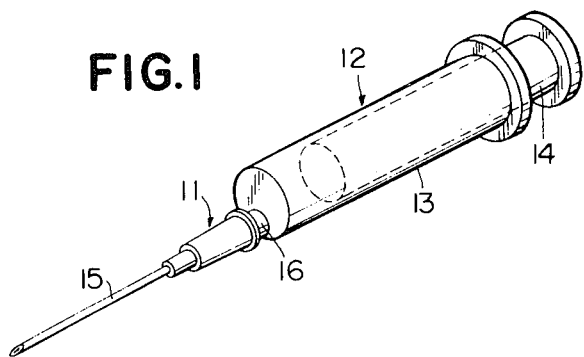
FIG. 1 is a perspective view showing a representative example of one type of medical administering liquid injector to which the present invention is applicable.
Figure 2:
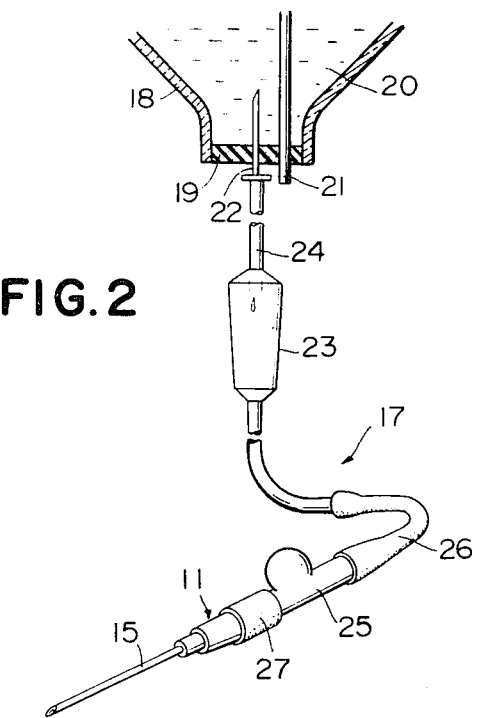
FIG. 2 is a perspective view showing a representative example of another type of medical administering liquid injector to which the present invention is applicable.

In FIG. 1, a needle holder device according to the present invention is designated in its entirety by reference numeral 11 and is shown as forming part of a syringe 12 which comprises, in addition to the needle holder device 11, a generally cylindrical hollow barrel 13, a piston 14 telescopically inserted into the barrel 13, and a pointed injection needle 15 which has its rearmost end portion fitted to the needle holder device 11 as shown. The syringe barrel 13 has a snout portion 16 at its leading end and the needle holder device 11 is detachably mounted on the snout portion 16 so that a continuous liquid conducting path is provided between the internal space or bore in the barrel 13 and the passageway in the injection needle 15. Alternatively, the needle holder device according to the present invention may be used as part of a medical administering dripset whose major parts and portions are illustrated in FIG. 2. Referring to FIG. 2, the dripset designated in its entirety by reference numeral 17 is used in combination with a Bayer bottle 18 which is shown inverted with its neck portion at the bottom. The Bayer bottle 18 has its neck portion closed by a rubber plug 19 and has stored therein a liquid medicament 20 such as for example an isotonic sodium chloride solution. Designated by reference numeral 21 is an air vent conduit or pipe which upwardly projects through the rubber plug 19 into the bottle 18 for providing communication between the atmosphere and the open space (not shown) above the surface of the stored liquid 20. The dripset 17 comprises a needle 22 projecting through the rubber plug 20 into the neck portion of the Bayer bottle 18. The needle 22 is in constant communication with a liquid reservoir 23 by way of a conduit 24 and the liquid reservoir 23 in turn is in communication with an adapter 25 through a flexible conduit 26. If desired, the conduit 26 may be connected direct to the needle 22. The needle holder device 11 according to the present invention is detachably fitted to the leading end portion of the adapter 25 by means of a tubular fitting 27.

The medical administering injectors of the above described natures are familiar not only to those skilled in the art but to laymen and, thus, description regarding the further detailed constructions and usages thereof will not be herein incorporated.

Figure 3:
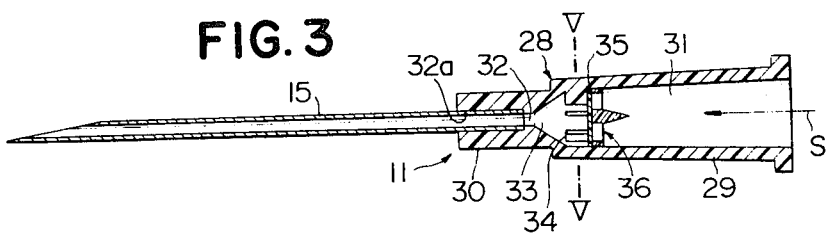
FIG. 3 is a longitudinal sectional view showing a first preferred embodiment of a needle holder device according to the present invention.

Turning to FIGS. 3 and 4, there is shown a first preferred embodiment of the needle holder device 11 according to the present invention which is thus applicable to the above described syringe 12 or dripset 18. The needle holder device 11 comprises a generally tubular member 28 which is shown consisting of a slightly tapering main body portion 29 and a tip portion 30 projecting forwardly from the main body portion 29. The tubular member 28 is formed with a passageway which is continuous between the opposite ends of the tubular member. The passageway consists of a generally cylindrical first bore portion 31 formed in the main body portion 29 and open at the rearmost end of the body portion, a generally cylindrical second bore portion 32 formed in the tip portion 30, terminating at the foremost end of the tip portion and smaller in diameter than the first bore portion 31, and a generally frusto-conical third bore portion 33 between the first and second bore portions 31 and 32. The frusto-conical third bore portion 33 is continuously reduced in diameter from its enlarged axial end adjacent to the first bore portion 31 toward its reduced axial end adjacent the second bore portion 32. The first, second and third bore portions 31, 32 and 33 have respective center axes which are substantially in line with each other. The frusto-conical third bore portion 33 is shown to have at its reduced axial end adjacent to the second bore portion 32 a diameter which is equal to the diameter of the second bore portion 32. The third bore portion 33 is further shown to be formed partly in the main body portion 29 and partly in the tip portion 30 but, if desired, the same may be formed in its entirety in the main body portion 29 or in the tip portion 30, though not shown in the drawings. The second bore portion 32 has its leading end portion enlarged in diameter as indicated at 32a and has securely received therein a rear end portion of the injection needle 15. The above mentioned diameter equal to the diameter of the reduced axial end of the third bore portion 16 is the diameter of the second bore portion 15 at its rearmost end adjacent to the third bore portion. The injection needle 15 is formed with a liquid conducting passageway extending throughout the length of the needle and which has a diameter substantially equal to the diameter of the rearmost end of the second bore portion 32. The injection needle 15 has a pointed leading end portion as is customary.

The tubular member 28 is further formed with a plurality of radial projections 34 which project radially inwardly into the first bore portion 31 from the inner peripheral surface of the main body portion 29 and which are circumferentially spaced apart from each other about the center axis of the first bore portion 29. The radial projections 34 extend longitudinally in parallel with the center axis of the first bore portion 29 and have foremost longitudinal ends located on a common plane perpendicular to the center axis of the first bore portion 31 and adjacent to the enlarged axial end of the frusto-conical third bore portion 33 and rearmost longitudinal ends located on a common plane perpendicular to the center axis of the first bore portion 31 and spaced apart a predetermined distance from the enlarged axial end of the third bore portion 33 toward the open end of the main body portion 29. Preferably, the radial projections 34 are arranged substantially in symmetry and are thus equidistantly spaced apart from each other about the center axis of the first bore portion 31, as will be seen from FIG. 5 in which the projections 34 are shown provided as five in number by way of example.

The needle holder device 11 further comprises a filter assembly which is held in position within the first bore portion 14 as shown in FIG. 3. The filter assembly includes a disc-shaped filter element 36 and a filter retaining element 36. As will be best seen in FIG. 6A, the filter retaining elemen 36 consists of a circular rim portion 37, a suitable number of radial limb portions 38 (shown provided as four in number by way of example) which radially inwardly extend from the rim portion 37 and which are angularly spaced apart from each other about the center axis of the rim portion, a central portion 39 containing the center axis of the rim portion 37 and conjoining the limb portions 38 together, and a conical projection 40 projecting axially from the central portion 39 and having a pointed or otherwise reduced leading end. The filter retaining element 36 is thus formed with generally sector-shaped open spaces 41 each of which is defined between neighbouring two of the limb portions 38 as the radii and which has a center axis coincident with the center axis of the rim portion 37. Preferably, the limb portions 38 are substantially equiangularly spaced apart from each other about the center axis of the rim portion 37 so that the sector-shaped open spaces 41 therebetween are substantially congruent with each other. The filter element 35 has a circumferentially marginal portion of one end face thereof closely received on the radial projections 34 at the previously mentioned rearmost longitudinal ends of the projections and has received on the other end face thereof the rim portion 37, limb portions 38 and central portion 39 of the filter retaining element 36, which thus has its conical projection 40 directed opposite to the frusto-conical third bore portion 33, viz., rearwardly in the first bore portion 31, as seen in FIG. 3. The filter element 36 and the rim portion 37 of the filter retaining element 36 have their respective outer peripheral edges closely received on the inner peripheral surface of the main body portion 29 of the tubular member 28. The conical projection 40 preferably has its pointed leading end located in line with the center axis of the rim portion 37, and the center axis of the rim portion 37, in turn, is preferably coincident with the center axis of the first bore portion 31. The conical projection 40 of the filter retaining element 36 in the embodiment of FIGS. 3 and 4 is assumed to have a circular cross section as shown in FIG. 7A. If desired, however, the central portion 39 and the conical projection 40 aligned with the former may be formed with continuous grooves 42 each extending between the pointed leading end of the conical projection 40 and the remoter end of the central portion 39 through each of the sector-shaped open spaces 41, as illustrated in FIG. 6B. In this instance, each of the grooves 42 preferably has a generally arcuate cross section as will be better seen from FIG. 7B. While, furthermore, the limb portions 38 have been assumed as four in number by way of example so that the four sector-shaped open spaces 41 have generally quadrantal configurations as will be best seen from FIG. 8A, the filter retaining element 36 may be formed with two, three or more than four limb portions as in FIG. 8B in which the filter retaining element designated by 36a is shown formed with three radial limb portions 38 which are substantially equiangularly spaced apart from each other about the center axis of the rim portion 37 so that three sector-shaped open spaces 41a each having a central angle of 120 degrees are formed therebetween. The limb portions 38 have been assumed to be equiangularly spaced apart from each other about the center axis of the rim portion 37, they may be angularly spaced apart through different angles from each other if desired.

The disc-shaped filter element 35 may be formed of a thin porous membrane or a sintered or otherwise compacted fiber mat of, for example, nylon fibers or may be replaced with a filter medium composed of a wad of at least one length of continuous filament of synthetic resin which is uniformly entwined into wad form. Such a filter medium is disclosed in U.S. Pat. No. 3,859,999 dated Jan. 14, 1975. On the other hand, the tubular member 28 and the filter retaining element 36 may be formed of any materials such as synthetic resins insofar as the materials are acceptable from both medical and chemical standpoints.

The needle holder device 11 thus constructed is fitted to the barrel 13 of the syringe 12 (FIG. 1) by inserting the snout portion 16 of the syringe barrel 13 into the main body portion 29 of the tubular member 28 until the snout portion 16 is closely received in the main body portion 29 or to the adapter 25 of the dripset 17 (FIG. 2) by inserting both the leading end portion of the adapter 25 and the main body portion 29 of the tubular member 28 into the tubular fitting 27 from the opposite open ends of the fitting until the adapter 25 and the tubular member 28 meet end-to-end in the fitting 27 or the former has its leading end portion closely received in the main body portion 29 of the tubular member 28. The tubular member 28 is shown in FIGS. 3 and 4 as having a flange at the rearmost end of the main body portion 29 but such a flange may be removed from the tubular member 28 to be used in the dripset 17. When the needle holder device 11 is thus fitted to the barrel 13 of the syringe 12 or to the adapter 25 of the dripset 17, a continuous liquid conducting path is provided between the bore in the syringe barrel 13 and the passageway in the injection needle 15 or between the internal space in the Bayer bottle 18 and the passageway in the injection needle 15 through the first, second and third bore portions 31, 32 and 33 constituting the passageway in the tubular member 28 of the needle holder device 11 and through the snout portion 16 of the syringe barrel 13 or the needle 22, conduit 24, reservoir 23, conduit 26 and adapter 25 of the dripset 17. When the piston 14 is thus moved forward in the syringe barrel 13 into which a liquid medicament or blood for transfusion has been introduced or the dripset 17 is arranged to be ready for feeding a liquid medicament from the Bayer bottle 18 into the adapter 25, then the liquid medicament or blood is forced to axially flow into the first bore portion 31 in the tubular member 28 of the needle holder device 11 in the direction indicated by arrow S in FIG. 3. For the sake of simplicity of description, the liquid medicament or the blood for transfusion will be hereinafter referred to simply as the liquid. The liquid thus entering the first bore position 31 initially flows in parallel with the center axis of the first bore portion 31. As the flow of the liquid approaches the filter assembly between the first and third bore portions 31 and 33, the center portion of the axial flow is diverged radially outwardly in a streamlined fashion by the conical projection 40 of the filter retaining element 36. The flow of the liquid is then split by the radial limb portions 38 of the filter retaining element 36 into four separate streams (or into three separate streams if the filter retaining element 36a of FIG. 8B is used), which are respectively passed through the individual sector-shaped open spaces 41 (or 41a in the filter retaining element of FIG. 8B) between the limb portions 38. The streams of the liquid are thereafter passed through the filter element 35 and are thus cleared of solid impurities initially contained in the liquid. The streams of the liquid which has been cleaned in this fashion meet each other in the third portion 33 downstream of the filter element 35. The flow of the liquid in the third bore portion 33 is smoothly squeezed or throttled as the flow advances forward because of the forwardly tapered configuration of the third bore portion 33. The flow of the liquid then enters the second bore portion 32 in the tip portion 30 of the tubular member 28 and is admitted from the second bore portion 32 into the passageway in the injection needle 15. Since, the initially axial flow in the first bore portion 31 is thus smoothly split into a plurality of separate but uniform streams by the conical projection 40 and the radial limb portions 38 of the filter retaining element 36 immediately before the flow reaches the filter element 35, the filter element 35 is enabled to pass the liquid therethrough uniformly throughout its working areas coextensive with the sector-shaped open spaces 41 in the filter retaining element 36. The filter element 35 is thus subjected to a liquid pressure which is uniformly distributed substantially throughout its total area. For this reason and further because of the fact that the filter element 35 per se is securely held in position relative to the tubular member 28 by means of the filter retaining element 36, the filter element 35 is prevented from being locally deformed or dislodged from its original position. Since, moreover, the liquid emerging from the filter element 35 is caused to flow in the forwardly tapered third bore portion 33, a streamlined laminar flow is established in the third bore portion 33 so that the liquid is enabled to smoothly flow from the third bore portion 33 into the second bore portion 32 and, as a consequence, from the first bore portion 31 into the third bore portion 22 through the filter element 35. This prevents the filter element 35 from being subjected to an undue force which might be created if turbulent flows are introduced downstream of the filter element 35 as is the case with a conventional needle holder device in which the cylindrical first bore portion 31 directly merges into the cylindrical second bore portion 32 or in which a bore portion provided between the first and second bore portions 31 and 33 also has a generally cylindrical configuration.

Figure 9:
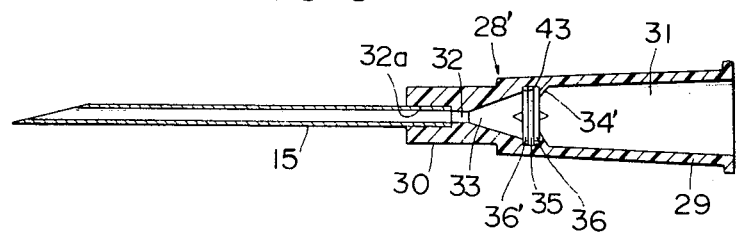
FIG. 9 is a longitudinal sectional view showing a second preferred embodiment of the needle holder device according to the present invention.
Figure 10:
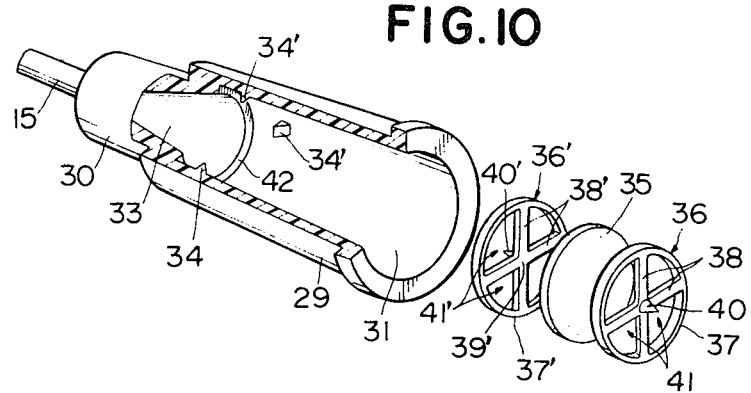
FIG. 10 is a partially cut-away perspective view of the needle holder device illustrated in FIG. 9.

FIGS. 9 and 10 illustrate a modification of the hereinbefore described element of the needle holder device according to the present invention. While the embodiment which has been described is adapted for an operation to discharge a medical solution or blood therefrom rather than for an operation to suck in a medical solution or blood from an ampoule or other sources, the embodiment illustrated in FIGS. 9 and 10 is adapted for both of such operations.

Referring to FIGS. 9 and 10, the needle holder device 11 comprises a generally tubular member 28' which is configured essentially similarly to its counterpart in the embodiment illustrated in FIGS. 3 and 4. The tubular member 28' thus comprises a main body portion 29 and a tip portion 30 and is formed with generally cylindrical first and second bore portions 31 and 32 and a generally frusto-conical third bore portion 33 between the first and second bore portions 31 and 32. Different from the tubular member 28 of the embodiment of FIGS. 3 and 4, the tubular member 28' is formed with an annular internal surface portion 43 at the foremost end of the first bore portion 31 adjacent to the third bore portion 33. The inner circumferential end of the annular surface portion 43 is coincident with the perimeter of the enlarged axial end of the third bore portion 33, which therefore has at the enlarged axial end a diameter smaller than the diameter of the first bore portion 31. Similarly to the tubular member 28 of the first embodiment, furthermore, the tubular member 28' is formed with a plurality of radial projections 34' which project inwardly into the first bore portion 31 from the inner peripheral surface of the main body portion 29 and which are circumferentially spaced apart from each other preferably equidistantly about the center axis of the first bore portion 31. While the radial projections 34 of the tubular member 28 of the first embodiment have their foremost longitudinal ends located adjacent the enlarged axial end of the third bore portion 33, the radial projections 34' of the second embodiment have first or front end faces contained in a common plane which is perpendicular to the center axis of the first bore portion 31 and which is spaced apart a predetermined distance from the enlarged axial end of the third bore portion 33 away from the third bore portion 33. The radial projections 34' thus arranged have second or rear end faces which are preferably inclined radially inwardly in the first bore portion 31 and toward the third bore portion 33 so that each of the radial projections 34' has a substantially right-angled triangular section taken in longitudinal direction of the first bore portion 31.

The needle holder device illustrated in FIGS. 9 and 10 further comprises a filter assembly which is closely held in position between the above described annular internal surface portion 43 and the radial projections 34' thus arranged. The filter assembly comprises a disc-shaped filter element 35 and first and second filter retaining elements 36 and 36' which are axially spaced apart from each other with the filter element 35 closely received therebetween. The filter element 35 is similar to its counterpart in the embodiment of FIGS. 3 and 4 and likewise each of the filter retaining elements 36 and 36' is configured similarly to the filter retaining element 36 in the embodiment of FIGS. 3 and 4. Thus, the second filter retaining element 36' consists of a circular rim portion 37', radial limb portions 38' radially inwardly extending from the rim portion 37' and equiangularly spaced apart from each other about the center axis of the rim portion 37', a central portion 39' containing the center axis of the rim portion 37' and conjoining the limb portions 38' together, and a conical projection 40' projecting axially from the central portion 39' and having a pointed foremost end. If desired, each of the first and second filter retaining elements 36 and 36' may have formed in its central portion and conical projection grooves (not shown) which are similar to the grooves 42 illustrated in FIG. 5B. The second filter retaining element 36' is thus formed with generally sector-shaped open spaces 41' between the limb portions 38' similarly to the filter retaining element 36. The first filter retaining element 36 is in close contact with one or rear end face of the filter element 35 with its conical projection 40 directed away from the filter element 36 and the second filter retaining element 36' is in close contact with the other or front end face of the filter element 35 with its conical projection 40' directed in opposite direction to the conical projection 40 of the first filter retaining element 36. The combination of the filter element 35 and the filter retaining elements 36 and 36' is held in position between the above mentioned annular internal surface portion 43 and the radial projections 34' in such a manner that the first filter retaining element 36 has its rim portion 37 closely received on the previously mentioned front end faces of the radial projections 34' and its conical projection 40 directed rearwardly in the first bore portion 31, viz., axially away from the third bore portion 33 and the second filter retaining element 36' has its rim portion 37' closely received on the annular internal surface portion 43 of the tubular member 28 and its conical projection 40' forwardly projecting into the third bore portion 33 through the enlarged axial end of the bore portion 33. The filter element 35 and the first and second filter retaining elements 36 and 36' thus arranged have their respective outer peripheral edges held in close contact with the inner peripheral surface of the tubular member 28 as will be seen from FIG. 9. The respective center axes of the rim portions 37 and 37' of the first and second filter retaining elements 36 and 36' and accordingly the respective central portions 39 and 39' and the respective conical projections 40 and 40' of the retaining elements 36 and 36' are preferably in line with each other and more preferably in line with the center axis of the first bore portion 31. In this instance, it is preferable that the first and second filter retaining elements 36 and 36' be positioned relative to each other in such a manner as to have their respective radial limb portions 38 and 38' in registry with each other across the filter element 35 in the axial direction of the first bore portion 31 so that the respective open spaces 41 and 41' in the elements 36 and 36' are substantially coextensive with each other in the axial direction of the bore portion 31.

The filter assembly thus arranged can be mounted in the tubular member 28 by inserting the second filter retaining element 36', filter element 35 and first filter retaining element 36 either one by one in this sequence or as a sub-assembly into the first bore portion 31 from the open rear end of the main body portion 29 and thereafter elastically press fitting the elements into their respective proper positions beyond the radial projections 34' on the inner peripheral surface of the main body portion 29. It is, thus, preferable to have the filter element 35 and the filter retaining elements 36 and 36' formed of elastic materials so that the individual elements are slightly deformable when they are forced against the projections 34'.

The needle holder device 11 thus constructed and arranged is adapted to achieve the previously described advantages of the first embodiment not only when used for an operation to discharge a medical solution or blood therefrom but when used for an operation to draw a medical solution or blood thereinto from an ampoule or other sources. When the needle holder device 11 is used for an operation to suck in a medical solution or blood for transfusion, the liquid is caused to flow from the third bore portion 33 into the filter element 35 through the individual open spaces 41' in the second filter retaining element 36' and is withdrawn from the filter element 35 into the first bore portion 31 through the individual open spaces 41 in the first filter retaining element 36. The solid impurities initially contained in the liquid are thus collected in major proportion on the front end face of the filter element 35. If the same needle holder device is then used for an administering operation, the solid particles collected by the filter element 35 will be released from the filter element back into the liquid flowing in a reverse direction from the filter element 35 into the third bore portion 33 and allowed into the body tissues into which the liquid is injected. To prevent this from occurring, the needle holder device once used for the suction of a medical solution or blood for transfusion should be replaced with a new one prior to administering operation.

While a few preferred embodiments of the present invention have been described and shown, such embodiments are merely illustrative of the gist of the present invention and may therefor be modified in numerous manners if necessary. For instance, the embodiment illustrated in FIGS. 3 and 4 may be modified so that the filter assembly is located on the opposite side of the radial projections 34 with the filter retaining element 36 positioned on the closer side of the filter element 35 to the third bore portion 33 and with the conical projection 40 directed into the third bore portion 33. In this instance, the radial projections 34 should preferably be axially spaced apart a suitable distance from the enlarged axial end of the third bore portion 33 so as to provide an ample space for accommodating the filter assembly between the enlarged axial end of the third bore portion 33 and the radial projections 34. The needle holder device arranged in this fashion is adapted for an operation to suck in liquid from an ampoule or any other source. Similar arrangement may be also achievable if the first filter retaining element 36 is removed from the embodiment of FIGS. 9 and 10 and the radial projections 34' are arranged to be in direct contact with the rear face of the filter element 35. It should be borne in mind that the modified constructions of the above described natures are also included in the scope of the present invention, although such constructions have not been illustrated in the accompanying drawings. While, furthermore, the filter assembly forming part of a needle holder device has been described and shown to comprise only one filter element, the filter assembly may comprise two or more filter elements having different thicknesses and/or different densities. Examples of such a modified filter assembly is disclosed in the same applicant's copending U.S. Pat. Application Ser. No. 694,794 filed June 10, 1976.

The features of the present invention are advantageous especially when incorporated into a needle assembly of the disposable type but may be applied to a needle assembly of the type adapted for repeated use if the filter element incorporated into the needle holder device is arranged to be changeable with a new one each time the needle holder device to be put to use.

What is claimed is:

1. A needle holder device to form part of a medical administering liquid injector, comprising a generally tubular member formed with a longitudinal passageway extending between the opposite ends of the tubular member and consisting of a generally cylindrical first bore portion terminating at one end of the tubular member, a generally cylindrical second bore portion terminating at the other end of the tubular member and smaller in diameter than said first bore portion, the second bore portion being adapted to receive therein an end portion of an injection needle to be mounted on the holder device, and a generally frusto-conical third bore portion between the first and second bore portions and continuously reduced in diameter from its enlarged axial end adjacent the first bore portion toward its reduced axial end adjacent to the second bore portion, said first, second and third bore portions having respective center axes which are substantially in line with each other, and a filter assembly held in position within said first bore portion, said filter assembly including at least one filter element having its entire peripheral edge received on the inner peripheral surface of the tubular member and filter retaining means in contact with at least one end face of said filter element and formed with at least two open spaces providing communication between said first and third bore portions through said filter element, said filter retaining means including at least one generally tapered projection extending in a direction substantially parallel with the center axis of said first bore portion and passing through the center axis of said open spaces.

2. A needle holder device as set forth in claim 1, in which said filter retaining means comprises at least one filter retaining element including a circular rim portion having its outer peripheral end on the inner peripheral surface of said tubular member and having a center axis, at least two radial limb portions extending radially inwardly from said rim portion and angularly spaced apart from each other about the center axis of the rim portion, and a central portion containing from the center axis of the rim portion and conjoining said radial limb portions, said rim portion, said limb portions and said central portion being in contact with one end face of said filter element and forming said open spaces therebetween, said tapered projection axially extending from said central portion away from said filter element.

3. A needle holder device as set forth in claim 2, in which said central portion and said tapered projection of said filter retaining element are formed with continuous grooves each extending between the reduced end of said tapered projection and the remoter end of said central portion through each of said open spaces between the radial limb portions.

4. A needle holder device as set forth in claim 3, in which each of said grooves has a generally arcuate cross section.

5. A needle holder device as set forth in claim 2, in which said tubular member is further formed with a plurality of radial projections radially inwardly projecting into said first bore portion from the inner peripheral surface of the tubular member and circumferentially spaced apart from each other about the center axis of said first bore portion, said radial projections having longitudinal ends on a common plane perpendicular to the center axis of said first bore portion and axially spaced apart from the enlarged axial end of said third bore portion, the radial projections receiving said filter assembly at said longitudinal ends.

6. A needle holder device as set forth in claim 5, in which said filter assembly is located on the remoter side of said radial projections from said third bore portion.

7. A needle holder device as set forth in claim 6, in which said filter element has a circumferential marginal portion of one end face thereof received on said radial projections at said longitudinal ends, said filter retaining element being in contact with the other end face of the filter element.

8. A needle holder device as set forth in claim 7, in which said radial projections have other longitudinal ends located adjacent said enlarged axial end of said third bore portion.

9. A needle holder device as set forth in claim 7, in which said filter element has its end face closer to said third bore portion received on said radial projections and its end face remoter from the third bore portion contacted by said filter retaining element.

10. A needle holder device as set forth in claim 9, in which said tapered projection of said retaining element axially projects in a direction opposite to said third bore portion.

11. A needle holder device as set forth in claim 7, in which said third bore portion has at its reduced axial end adjacent to said second bore portion a diameter which is substantially equal to the diameter of said second bore portion.

12. A needle holder device as set forth in claim 5, in which said filter assembly is located on the closer side of said radial projections to said third bore portion.

13. A needle holder device as set forth in claim 12, in which said filter retaining element has one end face of its rim portion received on said radial projections at said longitudinal ends of the projections and has the other end face thereof contacted by said filter element.

14. A needle holder device as set forth in claim 13, in which said rim portion of said filter retaining element has its end face remoter from said third bore portion received on said radial projections at said longitudinal ends of the projections and its end face closer to said third bore portion in contact with a circumferential marginal portion of that end face of said filter element which is remoter from said third bore portion.

15. A needle holder device as set forth in claim 14, in which said tapered projection of said retaining element axially projects from said central portion in a direction opposite to said third bore portion.

16. A needle holder device as set forth in claim 12, in which said filter retaining element has one end face located at said enlarged axial end of said third bore portion and the other end face in contact with said filter element.

17. A needle holder device as set forth in claim 16, in which said tapered projection of said retaining element axially projects into said third bore portion.

18. A needle holder device as set forth in claim 1, in which said filter retaining means comprises first and second filter retaining elements spaced apart from each other and receiving said filter element therebetween, each of the first and second filter retaining elements including a circular rim portion having its outer peripheral end on the inner peripheral surface of said tubular member and having a center axis, at least two radial limb portions extending radially inwardly from said rim portion and angularly spaced apart from each other about the center axis of the rim portion, and a central portion containing the center axis of the rim portion and conjoining said radial limb portions, said rim portion, said limb portions and said central portion forming said open spaces therebetween on each side of said filter element, said conical projection axially extending from said central portion away from the filter element, the tapered projection of the first filter retaining element extending in said first bore portion of each filter retaining element and the tapered projection of the second filter retaining element projecting into said third bore portion.

19. A needle holder device as set forth in claim 18, in which the respective central portions and the respective tapered projections of said first and second filter retaining elements are substantially in line with each other.

20. A needle holder device as set forth in claim 19, in which the limb portions of said first filter retaining element are substantially in registry with the limb portions of said second filter retaining element across said filter element.

21. A needle holder device as set forth in claim 18, in which said tubular member is further formed with a plurality of radial projections radially inwardly projecting into said first bore portion from the inner peripheral surface of the tubular member and circumferentially spaced apart from each other about the center axis of the first bore portion, said radial projections being longitudinally spaced apart from said enlarged axial end of said third bore portion a distance substantially equal to the thickness of said filter assembly and having first end faces closer to said third bore portion and second end faces remoter from the third portion, said filter assembly being held in position between said enlarged axial end of said third bore portion and said radial projections, said first filter element having one face in contact with one end face of said filter element and having its rim portion received on said radial projections at said first end faces thereof, said second filter retaining element having one end face in contact with the other end face of the filter element and the other end face located adjacent to said enlarged axial end of said third bore portion.

22. A needle holder device as set forth in claim 21, in which said first end faces of said radial projections are contained in a common plane perpendicular to the center axis of said first bore portion.

23. A needle holder device as set forth in claim 22, in which said second end faces of said radial projections are inclined radially inwardly in said first bore portion and toward said third bore portion, each of said radial projections having a substantially right-angled triangular section in longitudinal direction of the first bore portion.

24. A needle holder device as set forth in claim 21, in which said tubular member has an annular internal surface portion at the enlarged axial end of said third bore portion, said second filter retaining element having its rim portion in contact with said surface portion.

25. A needle holder device as set forth in claim 2, in which the center axis of said rim portion is substantially coincident with the center axis of said first bore portion.

26. A needle holder device as set forth in claim 2, in which said tapered projection has its reduced end substantially in line with the center axis of said first bore portion.

27. A needle holder device as set forth in claim 2, in which said radial limb portions are substantially equiangularly spaced apart from each other about the center axis of said rim portion.

28. A needle holder device as set forth in claim 5, in which said radial projections are substantially equidistantly spaced apart from each other.

29. A needle holder device as set forth in claim 2, in which said limb portions are provided as four in number.

30. A needle holder device as set forth in claim 2, in which said limb portions are provided as three in number.

31. A needle holder device as set forth in claim 1, in which said tubular member comprises a generally cylindrical main body portion and a generally cylindrical tip portion axially projecting from said main body portion, said first bore portion being formed in said main body portion and said second bore portion being formed in said tip portion.

32. A needle holder device as set forth in claim 31, in which said third bore portion is formed partly in said main body portion and partly in said tip portion.

33. A needle holder device as set forth in claim 31, in which said third bore portion is formed in its entirety in said main body portion.

34. A needle holder device as set forth in claim 31, in which said third bore portion is formed in its entirety in said tip portion.

35. A needle holder device as set forth in claim 31, in which said main body portion is adapted to be detachably fitted to the barrel of a syringe.

36. A needle holder device as set forth in claim 31, in which said main body portion is adapted to be detachably fitted to the adapter of a medical administering dripset.

* * * * *